United States Patent [19]
Kendall et al.

[11] Patent Number: 5,118,618
[45] Date of Patent: Jun. 2, 1992

[54] DIMETHYLGLYCINE ENHANCEMENT OF ANTIBODY PRODUCTION

[75] Inventors: Roger V. Kendall, Williston, Vt.; John W. Lawson, Clemson, S.C.

[73] Assignee: Foodscience Corporation, Essex Junction, Vt.

[21] Appl. No.: 649,524

[22] Filed: Feb. 1, 1991

Related U.S. Application Data

[63] Continuation of Ser. No. 416,761, Oct. 3, 1989, abandoned.

[51] Int. Cl.⁵ .................... C12P 21/08; C12N 5/02; C12N 5/16
[52] U.S. Cl. ............... 435/70.21; 435/240.27; 435/240.3
[58] Field of Search ............. 435/240.26, 240.27, 435/240.31, 70.21, 240.3; 935/108

[56] References Cited

U.S. PATENT DOCUMENTS

| | | | |
|---|---|---|---|
| 4,196,265 | 4/1980 | Koprowski et al. | 435/240.27 |
| 4,271,145 | 6/1981 | Wands et al. | 435/240.27 |
| 4,364,937 | 12/1982 | Kune et al. | 935/108 |

OTHER PUBLICATIONS

Graber et al., Immunomodulating Properties of Dimethyglycine in Humans J. Infectious Diseases, vol. 143, No. 1, pp. 101-105, 1981.
Tsiagbe et al., Poultry Sci. 66:1138-1146 and 66:1147-1154 (1987).
Gorski et al., FASEB. J. 5:2287-2291 (1991).
Wing-Keung et al., Immunobiology, 180:23-32 (1989).

*Primary Examiner*—John Doll
*Assistant Examiner*—George C. Elliott
*Attorney, Agent, or Firm*—Millen, White & Zelano

[57] ABSTRACT

N,N-dimethylglycine, along or in combination with mitogen, increases the antibody productivity of antibody-producing cell cultures.

18 Claims, No Drawings

DIMETHYLGLYCINE ENHANCEMENT OF ANTIBODY PRODUCTION

This is a continuation of application Ser. No. 07/416,761, filed Oct. 3, 1989, now abandoned.

BACKGROUND OF THE INVENTION

Kohler, G. and Milstein, C. (Nature 83:405-414 (1975)) described a technique for the production of antibodies of defined and predictable specificity by fusing spleen cells and myeloma cells. Recently, the importance and use of these monoclonal antibodies in biotechnology has dramatically increased. Their use has shown promise for the improvement of immunoassay sensitivities (Dalesevier et al., Clin. Chem. 27:1797-1806 (1981)). In addition, they are of great interest in the "missile therapy" field (Lessermann et al., Nature 293:226-228 (1981); Blythman et al., Nature 290:145-146 (1981), whereby drugs, such as anti-cancer agents, may be coupled to monoclonal antibodies which then specifically attack target cells (e.g., tumor cells) where they release the drug in situ. Much research dealing with the large scale production of monoclonal antibodies has been reported in recent years. However, antibody productivity by the fused cells or hybridomas is very low because of the slow growth or low secretion rate of the cells in culture medium. In the last 10 years, many reports detailing various methodologies for increasing monoclonal antibody productivity has been published. For example, electrical stimulation has been applied to hybridoma cells to activate metabolic activities and increase the monoclonal antibody production (Suzuki et al., Biochemica et Biophysica Acta 889:149-155 (1986). Factors have been described to enhance fusion of lymphocytes by mitogen stimulation of cells prior to fusion. Andersson and Melchers, Curr. Top. Microbiol. Immunol. 81:130-139 (1978) reported that after lipopolysaccharide (LPS) stimulation of mouse spleen cells, large blast cells fuse at least 10 times more frequently than the remaining small resting B cells.

N,N-dimethylglycine (DMG), which is a tertiary amino acid, is an intermediary metabolite found in low levels in many foods. It is produced in the body from choline and has been used as a non-fuel nutrient. In 1972, a report in the Russian veterinary medicine literature (Nizametidinova, G. A., Reports of the Kazan Veterinary Institute 112:100-104 (1972)) suggested that calcium pangamate was extremely effective in restoring immune competence to particulate antigen in X-ray irradiated guinea pigs and rabbits. Subsequent attention focused on DMG, a hydrolysis product of pangamic acid. DMG has been shown to be an effective modulator of the immune response in humans, by stimulating both humoral and cellular immunity (Graber et al., J. of Infect. Dis. 143:101-105 (1981)). In a double-blind study, human volunteers who received 120 mg of DMG (as the hydrochloride) orally per day demonstrated a four to five-fold increase in antibody production to the pneumococcal vaccine Pneumovax ® as compared with controls. The test group also had increased production of leukocyte inhibition factor, which indicated enhanced cellular immunity to vaccine antigen.

Previous studies in our laboratory by Reap and Lawson (personal communication), who investigated the ability of rabbits fed DMG to respond to different antigenic stimuli showed that DMG can stimulate both the humoral and cellular immune systems in rabbits.

SUMMARY OF THE INVENTION

In a method aspect, this invention relates to a method for increasing the production of antibodies in a nutrient culture of growing antibody-producing cells, comprising growing the cells in a culture medium containing an antibody production-stimulating amount of N,N-dimethylglycine or a biologically acceptable salt thereof. In a preferred aspect, the cells are monoclonal antibody-producing cells and more preferably are hybridomas.

In a composition aspect, this invention relates to a cell culture medium which comprises nutrients adapted for growth of the antibody-producing cells and an amount effective to increase the rate of antibody production by antibody-producing cells grown therein of N,N-dimethylglycine or a biologically acceptable salt thereof.

In a preferred composition aspect, this invention relates to a cell culture medium as defined above further comprising a mitogen and a method of cell culture production of antibodies which employ this medium.

Upon further study of the specification and appended claims, the objects and advantages of this invention will become apparent to those skilled in the art.

DETAILED DISCUSSION

In accordance with this invention, culture media are provided which contain an antibody production-stimulating amount (concentration) of N,N-dimethylglycine (DMG), e.g., from about 0.05 to 25 mg/ml of culture medium, preferably 0.25 to 5 mg/ml.

Examples of biologically acceptable salts of DMG which can be employed include nontoxic metal salts, including alkaline earth and alkali metals, e.g., Ca, Na and K, and mineral or organic acid addition salts, e.g., hydrochloride, sulfate, etc., wherein the acid moiety is that of a pharmaceutically acceptable acid.

Examples of suitable cell culture media for culturing antibody-producing cells are RPMI 1640 and DMEM media (Gibco, Grand Island, N.Y.).

Suitable antibody-producing cells include normal antibody producing cells isolated from, for example, spleen cells or blood cells of normal or immunized mammals, including man, mice, rats, and rabbits; myeloma 10 cells; hybridoma cells, which can be constructed by any of the known and conventional techniques; recombinant tissue culture cells containing cloned antibody genes; etc.

Suitable antibodies expressed by such antibody-producing cells include those directed to any antigen, whether naturally occurring or artificially constructed e.g., by conventional recombinant DNA techniques. Such antibodies are used, inter alia, for passive immunization, disease treatment, protein purification, immunoassay diagnostic tests, immunoaffinity chromatography, and other applications which require the use of antibodies, particularly antibodies directed to a specific antigen, and antibodies when required in significant amounts. Examples of such antibodies and cell lines producing them can be found in, for example, the American Type Culture Collection Catalog of Cell Lines and Hybridomas, published by the American Type Culture Collection, Rockville, Md., 1988 and updated periodically, from whom these cell lines can be purchased.

Even in a nutrient medium containing DMG in which myeloma and hybridoma cells are already rapidly proliferating, as shown in Example 5, it is possible to further increase the rate of antibody production by cell cultures containing non-immortal cell lines by adding a mitogen to the culture, thereby inducing the cells to more rapidly multiply.

Suitable mitogens which may be used in conjunction with DMG in increasing the production of antibodies include, for example, lipopolysaccharides, plant extract phytohemagglutinin, concanavalin A, pokeweed mitogen, tuberculin, and metal ions such as Hg or Zn. Antibody production-stimulating amounts of mitogen vary greatly depending upon the mitogen used, origin of the cells, etc., but are routinely determinable by one of ordinary skill in the art.

Except for the presence of added DMG and optionally also mitogen, the method of this invention employs the cell growth techniques and conditions conventionally employed to grow antibody-producing cells.

As is shown in Examples 2 and 3, hybridomas secreting the antibody to *Klebsiella pneumoniae* K43 or to Influenza A, Bangkok showed a significant increase in antibody titers, when cultured in vitro with DMG. The increase in antibody titer to *Klebsiella pneumoniae* K43 was much higher than that to Influenza A, Bangkok. In contrast, as shown in Example 4, when glycine was added to hybridoma cultures in place of DMG, no increase in antibody titers occurred. Thus, it appears that DMG itself and not glycine, which can metabolically be derived from DMG, is the compound which is responsible for increasing the titers.

The $^3$H-thymidine uptake study described in Example 5 was used to study whether the increase in antibody titers resulted from an increase in DNA synthesis. No increase in thymidine uptake was observed on addition of DMG to cultures of either hybridomas, myeloma cells, or spleen cells. Thus, the increase in antibody production was not due to an increase in DNA synthesis or cell proliferation. Although the increase in antibody production did not result from DMG stimulation of DNA synthesis, an influence on antibody synthesis or the antibody secreting mechanism was not ruled out.

Without further elaboration, it is believed that one skilled in the art can, using the preceding description, utilize the present invention to its fullest extent. The following preferred specific embodiments are, therefore, to be construed as merely illustrative, and not limitative, of the remainder of the disclosure in any way whatsoever.

In the foregoing and in the following examples, all temperatures are set forth uncorrected in degrees Celsius and, unless otherwise indicated, all parts and percentages are by weight.

The entire texts of all applications, patents and publications, if any, cited above and below, are hereby incorporated by reference.

EXAMPLES

Example 1

Production of Hybridomas

Preparation and Assay of Immunogen

Cultures of *Klebsiella pneumoniae* K43, obtained from the Food and Drug Administration (FDA), were maintained in nutrient broth. Immunogen was prepared by adding 0.25 ml of 40% formaldehyde to 20 ml suspensions of organisms in nutrient broth. The formalin-killed bacteria were washed twice with sterile 0.9% NaCl and stored at $-30°$ C. Protein concentration in the preparations were determined by the Bio-Rad protein assay.

Production of Hybridomas

BALB/c mice were immunized i.p. with 50 µg of formalin-killed *Klebsiella pneumoniae* K43 emulsified to Freund's complete adjuvant three times at biweekly intervals. Two weeks after the last i.p. injection, the mice were given an i.v. injection of 30 µg of the same antigen, followed by splenectomy 3 days later. The spleen cells were fused with the mouse myeloma cell line P3-X63-Ag8.653 (Kearney et al., J. Immunol. 123:1548–1550 (1973)) in the presence of 45% polyethylene glycol (MW 4,000, Sigma Chemical Co.). After HAT (hypoxanthine, aminopterin, and thymidine) selection, specific antibody secreting hybridomas were selected by enzyme-linked immunosorbent assay (ELISA). Four actively secreting monoclones designated 3A, 5F, 5D and 12F were selected after limiting dilution. Hybridomas were cultured in RPMI-1640 (Gibco Co.) supplemented with 15% fetal bovine serum (Sigma Chemical Co.) and 1% Antibiotic-Antimycotic (Sigma Chemical Co.) at 37° C. in 5% $CO_2$.

Enzyme-Linked Immunosorbent Assay

The stock solution of killed *Klebsiella pneumoniae* K43 and inactivated Influenza A, Bangkok (Merck, Sharp and Dohme) were diluted in 0.1M carbonate/bicarbonate coating buffer to a concentration of 6 µg/ml protein. Microtiter plate wells with antigen were coated overnight at 4° C. using 100 µl of buffer suspension per well. The plates were washed three times with assay buffer (0.02M phosphate-buffer saline pH 7.4 containing 0.1% gelatin and 0.05 v/v Tween 20). Supernatants either from anti-*Klebsiella pneumoniae* K43 hybridoma or anti-Influenza A, Bangkok hybridomas were then added to the wells in duplicate.

After incubation for one hour at 37° C. the plates were again washed three times with assay buffer and 100 µl antibody-enzyme conjugate (Sigma Chemical Co.) diluted one to 1000 in assay buffer were added to each well. After a further one hour incubation at 37° C., each well was emptied and washed three times with assay buffer. Then 100 µl of the enzyme substrate solution containing 25 ml 0.1M citric acid, 50 ml distilled $H_2O$, 40 mg o-phenylenediamine, 40 µl $H_2O_2$ (30% w/v) was added. The substrate was prepared fresh for each assay and kept in the dark until used.

The enzyme reaction was allowed to proceed for 30 minutes at 37° C. in the dark and then stopped by the addition of 50 µl 2.5M $H_2SO_4$ to each well. Optical densities (OD) were read at 490 nm using a Dynatech Minireader II spectrophotometer after setting the instrument to zero on a well containing substrate and $H_2SO_4$.

Results

Hybridomas which secrete antibody to *Klebsiella pneumoniae* K43 were obtained conventionally by fusing spleen cells from mice immunized with *Klebsiella pneumoniae* K43 and mouse myeloma cells in the presence of 45% polyethylene glycol according to the method of Kohler and Milstein, supra.

HAT was added to the culture medium to kill the non-fused myeloma cells and selected for hybridomas. Hybridomas secreting specific antibody were selected by measuring the antibody titers with ELISA. After limited dilution, four monoclones designated 3A, 5F, 5D and 12F were selected.

Example 2

Effect of DMG on Hybridomas Secreting Antibody to Klebsiella

DMG Dosage and Treatment

Anti-*Klebsiella pneumoniae* K43 hybridomas were cultured in RPMI-1640 supplemented with 15% fetal bovine serum and 1% Antibiotic-Antimycotic (complete medium) at 37° C. in 5% $CO_2$. Various concentrations of DMG (DaVinci Lab.) were added. The DMG previously filter sterilized was then added in 10 μl quantities to groups of 4 to 6 replicate wells to achieve final concentrations ranging from 0.25 to 6.25 mg/ml. After 2, 4 and 6 days, the supernatants from the hybridomas were removed and replaced with medium containing the identical concentration of DMG as originally added. The supernatants were measured by ELISA for antibody production.

Results

The four actively secreting monoclones were treated with various doses (0 to 5.0 mg/ml) of DMG at 2 day intervals for 6 days of culture. Antibody titers of the undiluted supernatants from the cultures were measured by ELISA. The results are shown in Tables I and II. The increase in antibody was calculated from the readings from DMG treated hybridomas minus the controls' and found to be statistically significant ($p<0.01$). As shown in Table III, the longer the period, up to 6 days, that the hybridomas were subsequently treated with DMG, the higher the amount of antibody that the hybridoma secreted. The data also indicated that the increase in antibody titers did not correlate with increase in DMG concentration within the experimental range (Table IV).

TABLE I

Average ELISA readings[a] for antibody titers to *K. pneumoniae* in the supernatants of hybridomas treated with DMG.

| Day of test | DMG dose mg/ml | Clone 3A | 5F | 6D | 12F |
|---|---|---|---|---|---|
| 2 | 0 | 0.34 | 0.31 | 0.32 | 0.40 |
|  | 0.5 | 0.94 | 0.68 | 0.72 | 1.08 |
|  | 1.0 | 0.87 | 0.70 | 0.69 | 1.22 |
|  | 1.5 | 0.74 | 0.83 | 0.74 | 1.12 |
|  | 2.0 | 0.83 | 0.69 | 0.67 | 1.09 |
|  | 2.5 | 0.80 | 0.71 | 0.80 | 1.12 |
| 4 | 0 | 0.43 | 0.37 | 0.36 | 0.44 |
|  | 0.5 | 0.98 | 0.71 | 0.86 | 1.14 |
|  | 1.0 | 1.04 | 0.71 | 0.90 | 1.36 |
|  | 1.5 | 1.03 | 0.79 | 0.81 | 1.17 |
|  | 2.0 | 0.99 | 0.73 | 0.76 | 1.21 |
|  | 2.5 | 1.11 | 0.75 | 0.82 | 1.31 |
| 6 | 0 | 0.44 | 0.37 | 0.36 | 0.46 |
|  | 0.5 | 1.14 | 0.99 | 1.06 | 1.61 |
|  | 1.0 | 1.23 | 1.12 | 1.16 | 1.49 |
|  | 1.5 | 1.30 | 1.22 | 1.28 | 1.30 |
|  | 2.0 | 1.17 | 1.31 | 1.06 | 1.33 |
|  | 2.5 | 1.30 | 1.01 | 1.31 | 1.56 |

[a]ELISA readings were measured at 490 nm in a Dynatech Minireader II Spectrophotometer.

TABLE II

Mean ELISA readings of the increase[a] in antibody titers to *K. pneumoniae* in control and DMG treated hybridomas.

| Day of test | DMG dose mg/ml | mean[b] treated-control |
|---|---|---|
| 2 | 0.5 | 0.513[c] |
|  | 1.0 | 0.528 |
|  | 1.5 | 0.495 |
|  | 2.0 | 0.477 |
|  | 2.5 | 0.515 |
| 4 | 0.5 | 0.523 |
|  | 1.0 | 0.600 |
|  | 1.5 | 0.550 |
|  | 2.0 | 0.523 |
|  | 2.5 | 0.598 |
| 6 | 0.5 | 0.793 |
|  | 1.0 | 0.843 |
|  | 1.5 | 0.868 |
|  | 2.0 | 0.810 |
|  | 2.5 | 0.888 |

[a]ELISA reading of hybridomas treated with DMG minus control reading.
[b]The least square mean.
[c]Standard error = 0.047.

TABLE III

Mean ELISA readings of the increase[a] in antibody titers to *K. pneumoniae* in control and test clones with time (days).

| Day of test | mean[b] treatment-control |
|---|---|
| 2 | 0.506[c] |
| 4 | 0.559 |
| 6 | 0.840 |

[a]ELISA readings of hybridoma treated with DMG minus control reading (p 0.01).
[b]The least square mean.
[c]Standard error = 0.021.

TABLE IV

Mean ELISA readings of the increase[a] in antibody titers to *K. pneumoniae* in control and test clones with varying DMG concentration.

| Day of test | mean[b] treatment-control |
|---|---|
| 0.5 | 0.69[c] |
| 1.0 | 0.658 |
| 1.5 | 0.638 |
| 2.0 | 0.603 |
| 2.5 | 0.666 |

[a]ELISA reading of hybridoma treated with DMG minus controls.
[b]The least square mean.
[c]Standard error = 0.027.

Example 3

Effect of DMG on Hybridomas Secreting Antibody to Influenza

Results

A hybridoma cell line which secretes monoclonal antibody against Influenza A, Bangkok was obtained from the ATCC, Accession Number HB66 and cultured according to the conditions described in Example 1. Various concentrations of DMG (0 to 6.25 mg/ml) were added to hybridoma cultures over a period of 6 days as described in Example 2. As shown in Tables V-VI, the average ELISA readings increased significantly on the addition of DMG (0.25 to 5.0 mg/ml). But the addition of DMG up to 6.25 mg/ml did not increase the antibody titer (Table VII). No correlation was found between the increase in antibody and the time of DMG addition or the concentration of DMG (Tables V-VI and VII).

TABLE V

Average ELISA[a] readings of the antibody titers to influenza in supernatants of hybridomas treated with DMG.

| Day of test | DMG (mg/ml) | ELISA readings |
|---|---|---|
| 2 | 0 | 0.39 |
|  | 0.25 | 0.68 |
|  | 0.50 | 0.77 |
|  | 1.50 | 0.72 |
|  | 2.50 | 0.64 |
|  | 5.00 | 0.74 |
|  | 6.25 | 0.51 |
| 4 | 0 | 0.44 |
|  | 0.25 | 0.69 |
|  | 0.50 | 0.74 |
|  | 1.50 | 0.78 |
|  | 2.50 | 0.77 |
|  | 5.00 | 0.75 |
|  | 6.25 | 0.54 |
| 6 | 0 | 0.47 |
|  | 0.25 | 0.73 |
|  | 0.50 | 0.78 |
|  | 1.50 | 0.86 |
|  | 2.50 | 0.80 |
|  | 5.00 | 0.79 |
|  | 6.25 | 0.49 |

[a]ELISA readings were measured at 490 nm in a Dynatech Minireader II spectrophotometer.

TABLE VI

Mean ELISA readings of the increase[a] in antibody titers to influenza in control and test clones with time (days).

| Day of test | mean treatment-control |
|---|---|
| 2 | 0.269[c] |
| 4 | 0.284 |
| 6 | 0.266 |

[a]ELISA readings of hybridomas treated with DMG minus control readings
[b]The least square mean
[c]Standard error = 0.087

TABLE VII

Mean ELISA readings of the increase[a] in antibody titers to influenza in control and test clones with varying DMG concentrations.

| DMG dose mg/ml | mean[b] treatment-control |
|---|---|
| 0.25 | 0.268[c] |
| 0.50 | 0.339 |
| 1.50 | 0.351 |
| 2.50 | 0.291 |
| 5.00 | 0.306 |
| 6.25 | 0.086 |

[a]ELISA reading of hybridoma treated with DMG minus control reading. the increase of ELISA readings from DMA (0.25 to 5.0 mg/ml) treated hybridomas to control is significant (p < 0.01), however, the increase of 6.25 mg/ml DMG is not significant (p = 0.093).
[b]The least square mean.
[c]Standard error = 0.012.

Example 4

Comparing Glycine with DMG

Results

As an additional control, varying concentrations of glycine (Bio-Rad Co.) (0 to 6.25 mg/ml) were added to hybridomas culture over a 6 day period analogously to Example 2. DMG was added to similar hybridoma cultures for comparison. The results did not indicate that the addition of glycine could increase the antibody titer (Table VIII). Thus, glycine does not appear to be responsible for the increase in antibody production.

TABLE VIII

Average ELISA readings for antibody titers to influenza in the supernatants of hybridomas treated with DMG or glycine.

| Day of test | DMG (mg/ml) | ELISA reading | Glycine (mg/ml) | ELISA reading |
|---|---|---|---|---|
| 2 | 0 | 0.39 | 0 | 0.41 |
|  | 0.25 | 0.66 | 0.25 | 0.46 |
|  | 0.50 | 0.75 | 0.50 | 0.48 |
|  | 1.50 | 0.68 | 1.50 | 0.49 |
|  | 2.50 | 0.63 | 2.50 | 0.47 |
|  | 5.00 | 0.70 | 5.00 | 0.45 |
|  | 6.25 | 0.51 | 6.25 | 0.47 |
| 4 | 0 | 0.43 | 0 | 0.46 |
|  | 0.25 | 0.68 | 0.25 | 0.50 |
|  | 0.50 | 0.76 | 0.50 | 0.48 |
|  | 1.50 | 0.78 | 1.50 | 0.42 |
|  | 2.50 | 0.74 | 2.50 | 0.43 |
|  | 5.00 | 0.71 | 5.00 | 0.37 |
|  | 6.25 | 0.53 | 6.25 | 0.47 |
| 6 | 0 | 0.48 | 0 | 0.48 |
|  | 0.25 | 0.73 | 0.25 | 0.44 |
|  | 0.50 | 0.76 | 0.50 | 0.44 |
|  | 1.50 | 0.81 | 1.50 | 0.41 |
|  | 2.50 | 0.81 | 2.50 | 0.46 |
|  | 5.00 | 0.74 | 5.00 | 0.45 |
|  | 6.25 | 0.49 | 6.25 | 0.42 |

Example 5

$^3$H-Thymidine Incorporation Assay

Lymphocyte Isolation

BALB/c mice were immunized with Influenza A, Bangkok virus by the same procedure as for the production of hybridomas above. Spleens were removed after the last i.v. injection. Single cell suspensions were prepared with a homogenizer and were washed twice with RPMI-1640. The lymphocytes and monocytes were separated from polymorphonuclear leukocytes (PMN) and erythrocytes on a Histopaque-1077 (Sigma Chemical Co.) gradient as described by A. Boyum, Scan. J. Clin. Lab. Invest. 21, 70-89 (1968). The erythrocytes and PMN have a density that is greater than Histopaque and will sediment through the gradient on centrifugation. The density of Histopaque is greater than lymphocytes and monocytes; therefore, these cells will remain above the Histopaque.

Lymphocytes and monocytes were aspirated from the Histopaque-RPMI interface and washed in RPMI-1640. The final cell pellet was resuspended in RPMI-1640 supplemented with 1% Antibiotic-Antimycotic. Cell counts were determined using a hemocytometer and the cell concentration was adjusted to $2 \times 10^6$ cells/ml. Cells were cultured with complete medium at 37° C. in 5% $CO_2$.

Myeloma Cell Isolation

Myeloma cells may be isolated using standard, conventional techniques, or purchased from suppliers such as the National Cell Culture Collection, Washington, D.C.

$^3$H-Thymidine Incorporation Assays.

Hybridomas, myeloma cells and lymphocytes from spleens were suspended in complete medium at $2 \times 10^6$ cells/ml and 100 µl of the cell suspensions were added to 96-well plates. Various concentrations of filter sterilized DMG were added to the cells. Lipopolysaccharide (Escherichia coli serotype 0127:B8 Sigma Chemical Co.) was added to the cells as a positive control. The microculture plates were incubated at 37° C., in 5% CO₂ for 48 hours. One μCi of ³H-thymidine (sp. act. 6.7 Ci/mmol, ICN Biomedicals Inc.) was then placed in the wells and incubated for an additional 8 hours. The 8 hour pulse of ³H-thymidine was terminated by transferring the cells from each wells onto glass fiber filter strip (Cambridge Technology, Inc.) with a multiple sample harvester (Cambridge Technology, Inc.). Toluene-based scintillation fluid (DuPont) was added for counting two minutes in a Beckman liquid scintillation counter (Beckman Instrument Inc.).

Results

³H-thymidine was added to hybridoma cultures to study whether the DMG increased cell DNA synthesis. The DMG was added to hybridomas secreting antibody to Influenza A, Bangkok, myeloma cells and lymphocytes isolated from spleens from mice immunized with Influenza A, Bangkok. LPS was added in place of DMG as a positive mitogenic control. Negative controls were prepared without the addition of any mitogen to cultures. The data in Table IX show that rates for DNA synthesis in hybridoma and myeloma cell cultures were very high. The addition of LPS (50 μg/ml) to these culture did not increase the DNA synthesis. This observation may be due to the fact that the cells are already rapidly proliferating and the mitogen does not further increase DNA synthesis. By contrast, LPS did increase DNA synthesis in spleen cells. CPM in hybridomas, myeloma cells and spleen cells treated with DMG were not significantly different from the negative controls.

TABLE IX

Incorporation of ³H-thymidine by different cells treated with various concentrations of DMG and LPS.

| Additions | CPM[a] | | |
|---|---|---|---|
| | hybridoma | myeloma | spleen |
| DMG (mg/ml) | | | |
| 0.25 | 29,884 ± 976[b] | 69,853 ± 1371 | 2,015 ± 511 |
| 0.50 | 27,198 ± 5001 | 67,832 ± 1379 | 1,321 ± 224 |
| 1.50 | 22,305 ± 3152 | 68,339 ± 3470 | 1,479 ± 536 |
| 2.50 | 27,252 ± 4641 | 65,087 ± 4216 | 2,627 ± 579 |
| 5.00 | 20,297 ± 2799 | 59,141 ± 1690 | 1,675 ± 270 |
| 6.25 | 19,294 ± 517 | 53,668 ± 1690 | 1,681 ± 249 |
| LPS (50 μg/ml) | 29,676 ± 6844 | 68,585 ± 5741 | 18,351 ± 4589 |
| Control | 25,605 ± 5204 | 60,931 ± 5199 | 1,596 ± 148 |

[a]Counts per minute (CPM)
[b]Data expressed as the mean ± standard deviation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for increasing the rate of antibody production in vitro comprising by growing antibody-producing cells in a nutrient culture medium containing an antibody production-stimulating amount of N,N-dimethylglycine or a biologically acceptable salt thereof.

2. A method of claim 1, wherein the antibody-producing cells are monoclonal antibody-producing cells.

3. A method of claim 2, wherein the antibody-producing cells are hybridomas.

4. A method of claim 1, wherein the amount of dimethylglycine present in the cell culture medium is 0.05 to 6.25 mg/ml.

5. A method according to claim 1, wherein the medium further comprises a mitogen.

6. A method according to claim 5, wherein the mitogen is lipopolysaccharide.

7. A method according to claim 2, wherein the amount of dimethylglycine present in the cell culture medium is 0.05 to 6.25 mg/ml and wherein the medium further comprises a mitogen.

8. A method according to claim 7, wherein the antibody-producing cells are hybridomas and wherein the mitogen is a lipopolysaccharide.

9. A cell culture medium adapted for the growth of antibody-producing cells, comprising a nutrient culture medium containing N,N-dimethylglycine or a biologically acceptable salt thereof in an amount effective to increase the rate of antibody production by the antibody-producing cells grown therein.

10. A cell culture medium of claim 9, wherein the amount of N,N-dimethylglycine is 0.05 to 6.25 mg/ml.

11. A cell culture medium of claim 9, further comprising antibody-producing cells.

12. A cell culture medium of claim 11, wherein the cells are monoclonal antibody producing cells.

13. A cell culture medium of claim 12, wherein the antibody producing cells are hybridomas.

14. A cell culture medium of claim 13, wherein the amount of DMG therein is 0.05 to 6.25 mg/ml.

15. A cell culture medium of claim 9, further comprising a mitogen.

16. A cell culture medium of claim 15, wherein the mitogen is a lipopolysaccharide.

17. A cell culture medium according to claim 12, wherein the amount of dimethylglycine present in the cell culture medium is 0.05 to 6.25 mg/ml and wherein the medium further comprises a mitogen.

18. A cell culture medium according to claim 17, wherein the cells are hybridomas and wherein the mitogen is a lipopolysaccharide.

* * * * *

UNITED STATES PATENT AND TRADEMARK OFFICE
CERTIFICATE OF CORRECTION

PATENT NO. : 5,118,618

DATED : June 2, 1992

INVENTOR(S) : Roger V. KENDALL et al.

It is certified that error appears in the above-identified patent and that said Letters Patent is hereby corrected as shown below:

On the Title page, item [63],
   Under U.S. Application Data:

Reads - - - - Continuation of Ser. No. 416,761, Oct. 3, 1989, abandoned.
   Should read - - - - Continuation of Ser. No. 416,761, Oct. 5, 1989, abandoned.

Signed and Sealed this

Twentieth Day of July, 1993

Attest:

MICHAEL K. KIRK

*Attesting Officer*    Acting Commissioner of Patents and Trademarks